(12) United States Patent
Schmitt et al.

(10) Patent No.: US 6,187,270 B1
(45) Date of Patent: Feb. 13, 2001

(54) DEVICE AND METHOD FOR THE SEPARATION OF MAGNETIC MICROPARTICLES

(75) Inventors: Urban Schmitt, Oberhausen; Eberhard Maurer, Weilheim; Gunter Pappert, Starnberg, all of (DE)

(73) Assignee: Roche Diagnostics GmbH, Mannheim (DE)

( * ) Notice: Under 35 U.S.C. 154(b), the term of this patent shall be extended for 0 days.

(21) Appl. No.: 08/499,078

(22) Filed: Jul. 6, 1995

(30) Foreign Application Priority Data

Jul. 7, 1994 (DE) ................................. 44 23 878

(51) Int. Cl.[7] ........................ G01N 35/10; G01N 33/543; B01L 3/02
(52) U.S. Cl. ........................ 422/101; 422/63; 422/100; 436/43; 436/54; 436/174; 436/177; 436/180; 436/807; 210/222; 210/695
(58) Field of Search .................... 422/63–67, 100, 422/101; 436/43, 49, 47, 54, 174, 177, 180, 807, 809, 810; 210/695, 222, 223

(56) References Cited

U.S. PATENT DOCUMENTS

| | | |
|---|---|---|
| 3,985,649 * 10/1976 | Eddelman | 259/1 R |
| 4,292,920 * 10/1981 | Smith et al. | |
| 4,526,046 * 7/1985 | Oberli et al. | 73/864.16 |
| 5,013,529 * 5/1991 | Itoh | 422/100 |
| 5,160,378 * 11/1992 | Tuunanen et al. | 134/25.1 |
| 5,171,537 * 12/1992 | Wainwright et al. | 422/100 |
| 5,183,638 * 2/1993 | Wakatake | 422/64 |
| 5,200,084 * 4/1993 | Liberti et al. | 210/695 |
| 5,200,151 * 4/1993 | Long | 422/100 |
| 5,647,994 * 7/1997 | Tuunanen et al. | 210/695 |
| 5,702,950 * 12/1997 | Tajima | 439/49 |

FOREIGN PATENT DOCUMENTS

| | | |
|---|---|---|
| 0 272 915 A2 * | 6/1988 | (EP) . |
| 0 339 980 A1 * | 11/1989 | (EP) . |
| 0 687 501 A2 * | 12/1995 | (EP) . |
| 60-159651 | 8/1985 | (JP) . |
| 1-321363 | 12/1989 | (JP) . |
| 4-194752 | 7/1992 | (JP) . |
| WO 93/13400 * | 7/1993 | (WO) . |
| WO 95/00247 * | 1/1995 | (WO) . |

* cited by examiner

*Primary Examiner*—Long V. Le
(74) *Attorney, Agent, or Firm*—Arent Fox Kintner Plotkin & Kahn PLLC (57) ABSTRACT

The invention addresses a device for separating magnetic microparticles in a liquid with the aid of a magnetic field. During the separation procedure, the liquid containing the microparticles is located in the tip of the pipette. Moreover, the invention also addresses a method for separating microparticles, and a method for washing microparticles.

13 Claims, 6 Drawing Sheets

FIG. 4c  WASHING PROCEDURE 1

FIG. 4d  WASHING PROCEDURE 2

FIG. 5

DEVICE AND METHOD FOR THE SEPARATION OF MAGNETIC MICROPARTICLES

The present invention relates to a device and a method for the separation of magnetic microparticles from a suspension of magnetic microparticles in a liquid by means of a magnetic field. The device comprises a pipette, a pump connected to said pipette, a magnet, and a device for moving the pipette toward the magnet and away from it.

The separation of magnetic microparticles is used in particular in immunoassays and in DNA testing. Immunological reactions on the surface of coated, magnetic particles allow a simple separation of bound from free reaction partners as the magnetic particles are retained by the magnetic forces while the remaining reaction solution can be removed.

In prior art, the separation of coated magnetic particles has already been used to carry out immunoassays. European patent application EP-A-0 339 980 describes a device (FIGS. 10 and 11) used to separate a suspension of magnetic microparticles by means of a magnetic field. The particles are then separated on a special wire located in the inside of the reaction vessel. In order to release the microparticles from the wire, the latter is exposed to vibrations. A drawback of the device is that it requires the presence of high magnetic fields and the action of an agitator. The instrument described is also difficult to integrate in existing instrument concepts as neither strong magnets, nor shaking devices, nor agitators, nor special wires are present in conventional analyzers.

It was, hence, an object of the invention to provide a device and a method for separating and washing magnetic microparticles which could be easily integrated in existing instrument concepts and require only a small number of additional devices.

This object was accomplished by providing a device for the separation of magnetic microparticles from a suspension of magnetic microparticles in a liquid by means of a magnetic field. The device comprises a pipette, a pump connected to said pipette, a magnet, and a device for moving the pipette toward and away from said magnet, or a device for moving the magnet toward and away from said pipette while the magnetic microparticles are deposited at the inner wall of the pipette.

Numerous immunological assays have been simplified with the introduction of coated magnetic microparticles. In these processes, the magnetic particles assume the function of a solid phase. The use of magnetic microparticles is advantageous when the test to be carried out requires the separation of bound from non-bound reaction partners. Since immunological tests with magnetic microparticles are known in prior art (e.g. U.S. Pat. No. 4,219,335), the chemical and/or immunological aspect thereof is not discussed in further detail at this point.

Magnetic microparticles are understood to be microparticles that are attracted by means of a magnetic field. The magnetic particles can, hence, themselves be magnetized. Preferred materials are those that exhibit only a minor remanence. The material of the microparticles can be a compound material, e.g. a matrix that contains magnetically attractable particles. Magnetically attractable materials are, for example, iron, iron oxide, nickel, cobalt, or chromium oxide. One or several particles of this material can be embedded in a matrix. The matrix can consist of a multitude of materials, e.g. organic or inorganic polymers.

The present invention makes use of coated microparticles. The coating can be a polymer, for example, that carries reactive groups on its surface (U.S. Pat. No. 4,454,234) or is coated with a biologically active component (U.S. Pat. No. 4,177,253, U.S. Pat. No. 3,933,997). Both the manufacture of magnetic microparticles and their coating are known from prior art (U.S. Pat. No. 4,297,337, DE-A-3014036). Microparticles coated with biologically active groups are also commercially available, for example, by Dynal Tech and Rhône-Poulenc. The microparticles marketed by these companies have the advantage of having a relatively low density allowing the use of relatively large microparticles. An increasing density entails an increase in the sedimentation rate of the microparticles which then requires a reduction of the diameter of the microparticles in order to avoid an undesired separation of the suspension through gravity. The beads manufactured by Dynal have a diameter of 2.8 $\mu$m with a density of approximately 1.3. The microparticles manufactured by Rhône-Poulenc have a diameter of 0.5 to 2 $\mu$m with a density of also 1.3. If the beads manufactured by these firms are suspended in aqueous solutions, it takes hours to accomplish a separation through gravity.

These beads can therefore be used in analysis procedures without requiring additional equipment for shaking or generating ultrasound in order to keep the suspension stable.

An apparatus in accordance with the invention comprises a pipette to hold a suspension of magnetic microparticles. Pipettes usually have a cylindrical shape with an opening at each of their front sides. In connection with an apparatus of the invention, it is also possible to use pipettes which have areas with rectangular cross sections. It is essential to the invention that the interior of the pipette can be penetrated by a magnetic field, provided a magnet is set up at the outer wall of the pipette. The pipette material must, hence, be permeable to magnetic field lines with glass and plastic being usually employed as materials. In a preferred manner, the pipette has a cylindrical base onto which a plastic tip is placed. The liquid held in the pipette is located inside the tip where the separation of the magnetic microparticles is accomplished. The use of tips has the advantage that they can be discarded after use. The removal of possibly remaining beads is therefore not required. If possible, the interior of the pipette should not have any recesses or edges as this may interfere with a quantitative release of magnetic microparticles separated in the pipette. In a preferred manner, the cylinders for pipettes have relatively small diameters, approximately in the range of a few millimeters up to 2 cm. Pipettes that have a uniform inner diameter over their longitudinal extension are suitable; it is, however, advantageous to have pipettes with tapered ends.

The inner wall of a pipette should be smooth. It is also possible to use pipettes whose inner walls are provided with a non-adherent coating, for example, a silane coating.

In order to fill the pipettes with suspensions and solutions, one of their openings is connected to a pump. Both the elements to implement the coupling of the pipette to the pump as well as the pump itself are known in prior art on automated analyzers.

Magnets for separating the magnetic microparticles can be electrical magnets as well as permanent magnets. Permanent magnets are preferred as these do not generate heat during operation which could interfere with the analysis. Strong permanent magnets exhibit a magnetic flow that is sufficient to separate magnetic microparticles from a suspension with a thickness of up to a few centimeters. The magnets used preferably have the form of a bar magnet. It is, however, also possible to use magnets with various other shapes. The shape is usually selected such that only one magnetic pole is located in the vicinity of the pipette.

The surface of the magnet located in the vicinity of the pipette should have a cross section that is essentially not smaller than the diameter of the pipette. This magnet surface can be planar; a concave curvature of the surface is, however, preferred so that the magnet matches the surface area of the pipette. In a preferred manner, this concave surface is so small that it covers less than one half of the surface area of the pipette so that a highly inhomogeneous magnetic field is generated in the inside of the pipette.

The magnet can be fixed in its position inside the apparatus or attached to a device for moving it spatially. A fixed positioning of the magnet is preferred in accordance with the invention to simplify the structural design.

Further, a device in accordance with the invention comprises a device for moving the pipette. In commonly used analyzers, pipettes are already used that are attached to a multifreedom robot arm. Robot arms that are suitable for the invention are those that can be moved in one or two directions parallel to the basic surface of the analyzer and perpendicularly thereto. Moreover, Rz-arms are also suitable. They are able to carry out a rotating movement as well as a movement perpendicularly to the basic surface of the analyzer.

The device for moving the pipette serves to move the pipette toward the magnet and away from it. Principally, a sensor-controlled movement is also possible. However, due to the enormous technical complexity it is preferred that the movement of the pipette be programmed so as to have an optimal distance between pipette and magnet and between a subsequent relative movement of pipette and magnet. The invention is also intended to encompass an embodiment where the magnet is moved toward the pipette.

In order to deposit magnetic microparticles at the inner wall of the pipette, it is not necessary to have a fine adjustment of the distance between magnet and pipette. However, the closer the magnet approaches the pipette, the faster a quantitative separation occurs. The time required for a quantitative separation can be determined empirically based on the diminishing turbidity of the suspension. For use of the device in an automated analyzer, it is not necessary to determine the separation time for each assay. It is possible to set up a time-frame for a given device during which complete separation can be achieved for all liquids used. For special applications, it is, of course, also possible to provide a detection of the separation. This can be achieved, for example, by exposing the content of the pipette to a light beam and to detect the quantity of light that has passed.

The invention further addresses a method for washing magnetic microparticles comprising the following steps:

a) providing a suspension of magnetic microparticles in a first liquid,
b) transferring the suspension into a pipette,
c) moving the pipette toward the magnet or moving the magnet toward the pipette,
d) removing the first liquid from the pipette,
e) transferring a second liquid into the pipette,
f) removing the second liquid together with the microparticles suspended therein from the pipette into a collecting container.

The washing of magnetic microparticles in the course of an analysis procedure is necessary to remove non-bound reaction partners. Moreover, experience has shown that during storage, coated magnetic microparticles release parts of the coating. In order to enhance the accuracy of the analysis, it is therefore advantageous to wash the microparticles directly prior to their use in order to remove released particles of the coating.

The manufacturer already provides the magnetic microparticles in the form of a suspension. These suspensions exhibit the hydrodynamic properties of liquids and can, hence, be also drawn into a pipette as are liquids. This is done by immersing the open pipette tip into the suspension and reducing the internal pressure of the pipette via the pump to which the pipette is connected. Devices for pipetting defined quantities of liquids are known in prior art. These instruments are referred to as pipettors or diluters. In a preferred manner, the pipetting procedures carried out such that a small air bubble forms at the pipette tip. This is done to prevent droplets from dripping down from the pipette.

The pipette filled with the suspension is then moved toward a magnet in order to separate the microparticles or the magnet is moved toward the filled pipette. In a preferred manner, the magnet is attached at a place of the pipette wall which is only a few millimeters below the liquid level. If the magnet has a sufficient strength and if its surface extends far enough in direction toward the pipette tip, it suffices to fix the magnet in one position in order to separate the microparticles suspended in the liquid. If this is not the case, the magnet may be moved along the outer wall of the pipette in direction toward the pipette in order to ensure complete separation.

After the microparticles have been deposited at the inner wall of the pipette, the liquid from which the microparticles have been removed is ejected from the pipette. Now, a second liquid is drawn into the pipette to wash it. This can be done while the magnet is still at the wall of the pipette or, if this is not desired, the magnet can be moved away from the pipette prior thereto. In the first procedure, the separated magnetic microparticles are washed in the flow of the liquid passing by; in the second case the the microparticles are at least partly swirled up. The liquid in which the magnetic microparticles are suspended and the washing liquid may be water or an inert fluid. In a preferred manner, the liquids contain detergents as this increases the washing effect. It was surprising to see that resuspension of the separated microparticles is improved in liquids containing detergents and also that they can be more easily removed from the pipette when such liquids are used.

In a simple washing procedure, the microparticles can be ejected directly with the liquid. If another washing procedure is necessary, the microparticles can be suspended in the washing liquid according to the already described procedure and be again deposited at the wall.

The efficiency of a washing procedure depends on the extent of how the separated microparticles are resuspended in the washing liquid and if a quantitative ejection of microparticles from the pipette is possible. It is, hence, preferred to resuspend separated microparticles in the washing liquid. This can be achieved by removing the magnet from the pipette tip before the washing liquid is drawn into the pipette. The partial suspension resulting from swirling up can be enhanced by moving the magnet toward the pipette from the site which is opposite the site of separation. Magnetic microparticles that have been deposited at the wall can thus be removed from this wall. The effect of the magnet from the opposite side should not be allowed to last too long during this procedure as this may result in another separation of the magnetic microparticles. Instead of moving the magnet from the opposite side toward the pipette, it is also possible to turn the pipette itself around its longitudinal axis through the use of a rotating device of rotating means. In another configuration, a moving device or moving means can be provided to rotate the magnet around the longitudinal axis of the pipette. In order to resuspend separated magnetic microparticles, it is also possible to install a mechanical agitator or an ultrasound device. The described methods for resuspension can also be applied to eject the microparticles together with the liquid from the pipette. In a preferred manner, the removal of the microparticles from the pipette is accomplished by depositing the microparticles at a wall of the pipette and collecting them in the tip of the pipette by exposing pipette and magnet to a relative movement. To achieve this, the pipette is passed by the magnet in its longitudinal direction from the upper level of the liquid to its tip. Subsequently, the liquid is ejected from the pipette and the microparticles which have been accumulated at the outlet of the pipette tip are swept away.

The invention also addresses a method for carrying out an analysis comprising the steps of providing a suspension of magnetic microparticles in a first liquid, incubating the suspension with an analyte, transferring the reaction mixture in a pipette, moving the pipette toward the magnet or moving the magnet toward the pipette, ejecting the liquid phase from the pipette, transferring a system liquid into the pipette, moving the pipette away from the magnet, ejecting the system liquid together with the microparticles in a receiving container, and determining the analyte concentration based on the specific properties of the system liquid or the microparticles.

The already described methods for separating and washing microparticles can be used in an analysis procedure. In such an analysis, the magnetic microparticles are incubated together with an analyte, e.g. blood, plasma, serum, saliva, tissue fluid, urine. During the incubation, the substance of the analyte to be determined binds either directly or via a bonding agent to the coating of the microparticles. Possible methods for carrying out heterogeneous immunoassays and also the use of magnetic microparticles in these assays have been known from prior art; their detailed description is therefore omitted here.

The subsequent steps of an analysis procedure occur as described for the washing procedure. However, in the analysis procedure, a system liquid instead of a washing liquid is drawn into the pipette. Said system liquid can either be water or an inert liquid containing detergents, reagents, or auxiliary substances. Once the microparticles have been ejected from the pipette together with the system liquid, the analyte bound to the magnetic beads reacts with an immunologically active reagent, e.g. an antibody carrying a label (e.g. an enzyme, ruthenium label). In a preferred manner, the bound analyte is detected after it has been washed again with washing solutions that are conventionally used in immunological procedures. The analyte can be detected via a color reaction, for example. In a preferred manner, the microparticles are separated in a measurement cell where a measuring signal (coloration, fluorescence) is generated. The generation of an electrochemiluminescent reaction with the microparticles is particularly preferred. This is described in patent application WO 89/10551.

The following examples describe the invention in greater detail.

Figure 1:
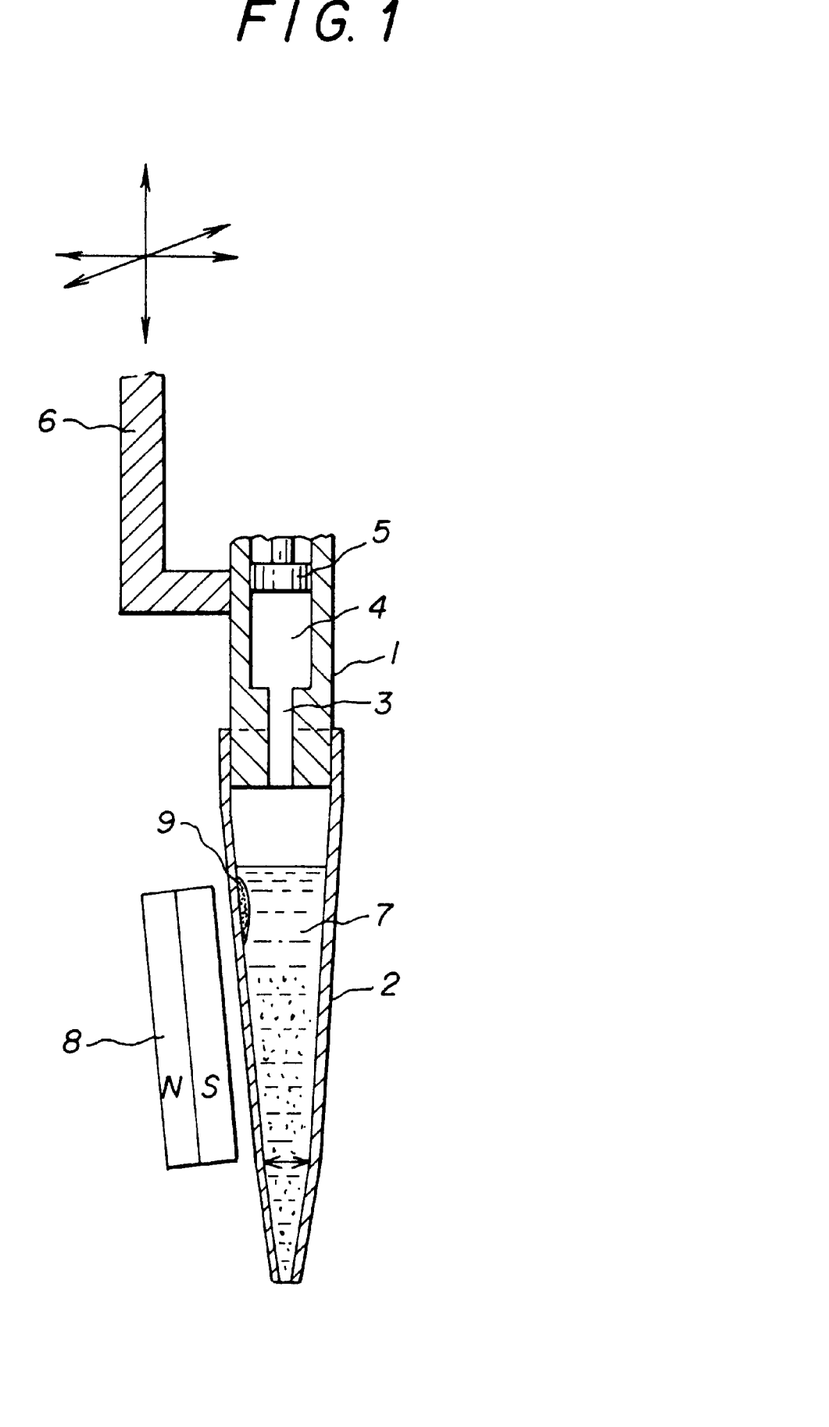
FIG. 1: Device for separating magnetic microparticles

FIG. 1 shows a device of the invention for precipitating and washing magnetic microparticles. The top part (1) of the pipette is a cylindrical metal body onto which the bottom part (2) of the pipette is placed. The bottom part (2) of the pipette is a plastic tip manufactured by Eppendorf. Both top and bottom part of the pipette are connected via a channel (3). A pumping device with pistons (5) and cylinders (4) is directly integrated in the top part (1) of the pipette. When the piston (5) is moved within the cylinder (4), a liquid (7) can be drawn into the pipette bottom part (2) or be removed therefrom. Pipette top (1) is mechanically connected to an X, Y, Z-arm (6) of an analysis instrument. The pipette can, hence, be moved in all three spatial directions. FIG. 1 also shows a magnet (8) located in the vicinity of an outer wall of the bottom part (2) of the pipette. Owing to the magnetic forces, microparticles (9) from the upper part of liquid (7) have been deposited at the inner wall of the bottom part (2) of the pipette.

Figure 2:
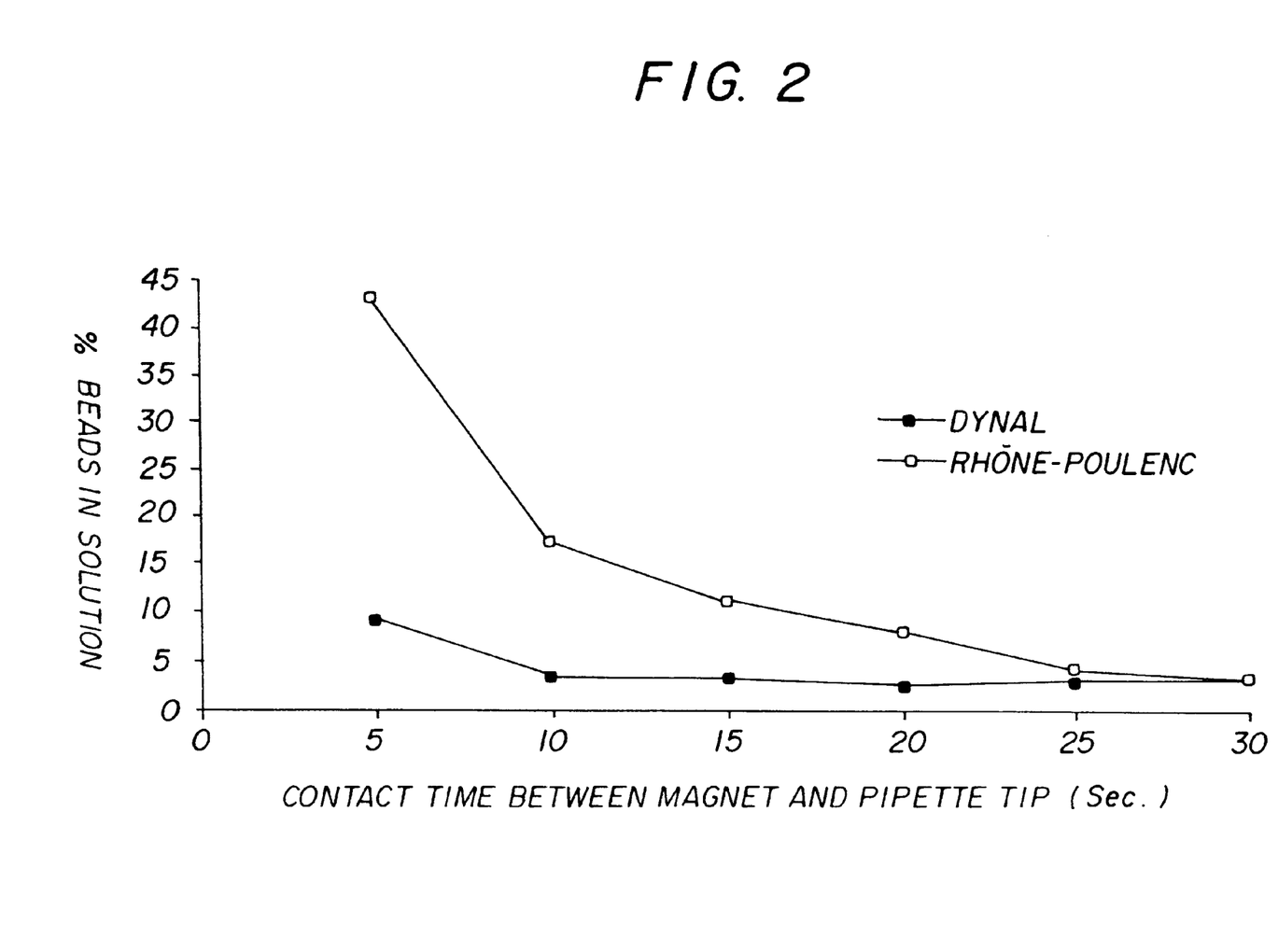
FIG. 2: Time required for separation with different microparticles

FIG. 2 shows the time required for separating various microparticles in a pipette with a max. inner diameter of 4 mm. The magnet used was a bar magnet with a magnetic flow density of approx. 2 gauss. The surface of the magnet moved toward the pipette was 15 mm×5 mm. The portion of beads remaining in the suspension that was found on the Y-axis was determined in that the magnet was moved toward the bottom part of the pipette for a time indicated on the X-axis. After this time, the suspension was ejected from the pipette. The beads remaining in the suspension were detected in an immunological reaction.

Beads manufactured by Dynal have a diameter of 2.8 $\mu$l while the diameters of microparticles manufactured by Rhône-Poulenc range between 0.5 and 2 $\mu$m. From FIG. 2, it can be understood that irrespective of the type of beads used, an approximately quantitative separation could be accomplished after a sufficient period of time.

Figure 3:
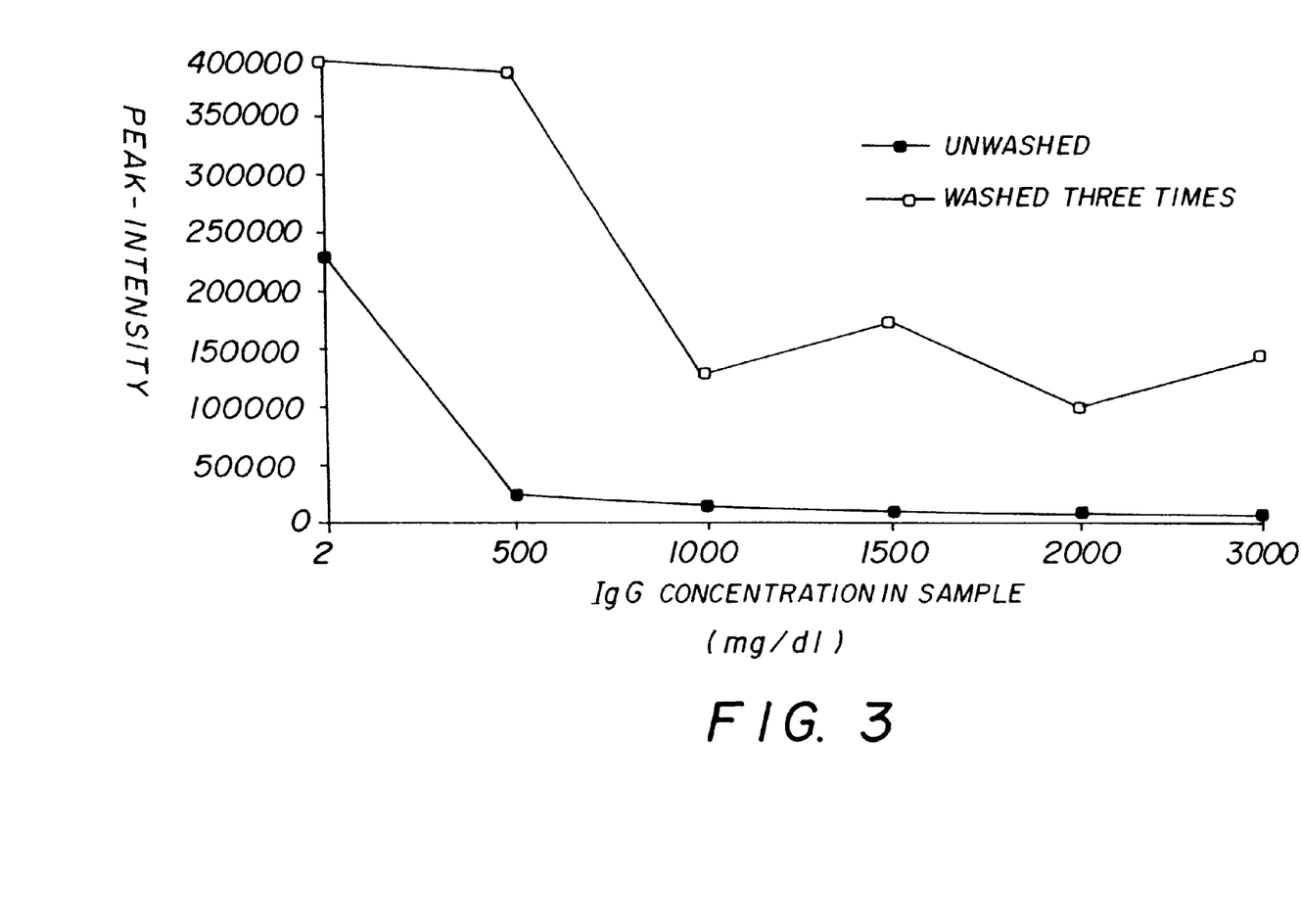
FIG. 3: Effects of bead washing on the sensitivity of an immunoassay

FIG. 3 shows the effect of the washing procedure on the sensitivity of an immunoassay. In this experiment, streptavidin-coated beads by Dynal were used.

In order to carry out the experiments, 50 $\mu$l buffer containing a suspension of Dynal streptavidin beads (600 $\mu$g beads/ml) were provided in a reaction vessel. Subsequently, 40 $\mu$l hepatitis C virus antigens coupled with biotin were added. The mixture was incubated for 25 minutes at 37° C. with 10 $\mu$l sample of hepatitis C virus-containing serum with different IgG contents.

Figure 4A:
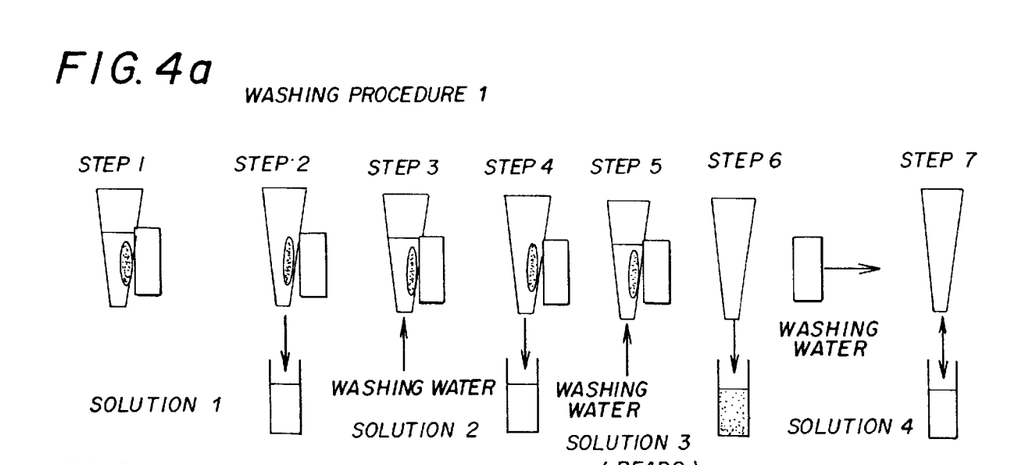
FIGS. 4a to 4d: Washing procedure for beads.
Figure 4B:
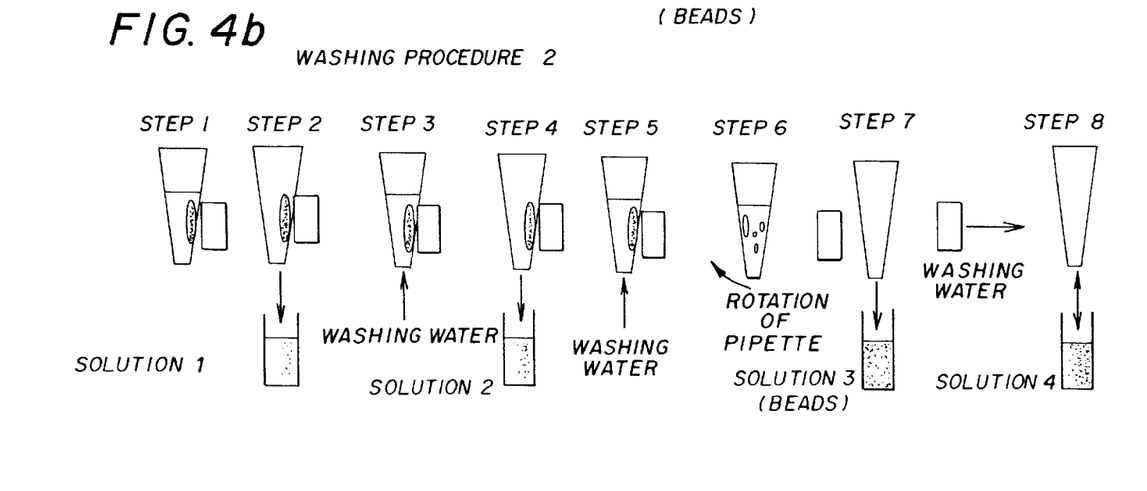
Figure 4C:
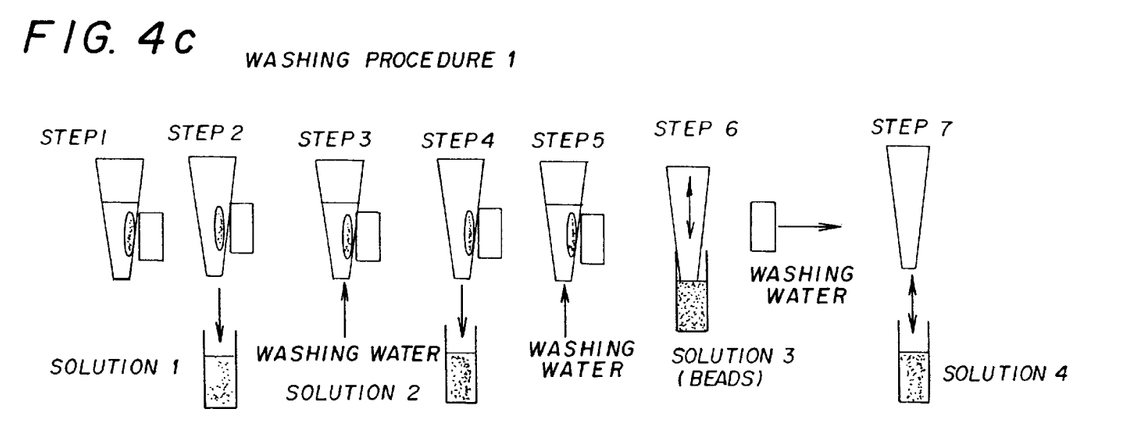
Figure 4D:
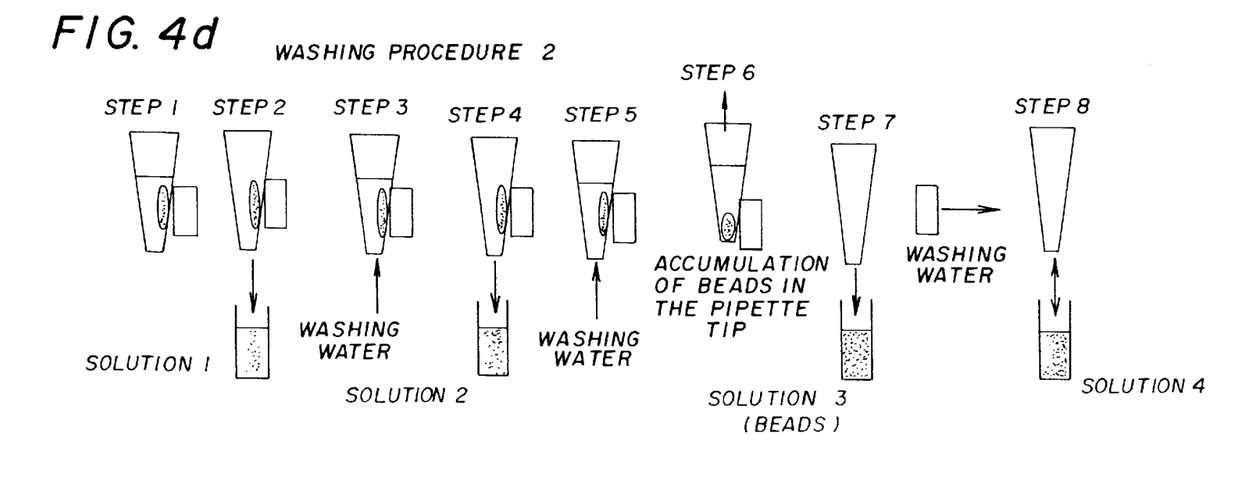

The beads were washed according to the method described in FIG. 4d. When the quantity of beads was transferred into a reaction vessel, 50 $\mu$l buffer and polyclonal antibodies to human IgG (from sheep) labeled with ruthenium were added. In order to detect the ruthenium label, the electrochemiluminescent radiation was measured with the arrangement described in WO 89/10551.

FIGS. 4a to 4d show possible methods for washing beads. In order to separate the beads, a pipette with a 100 $\mu$l tip was used. The pipette was fixed in its position and a strong permanent magnet was set up with the aid of a guide rail always at a defined height to the wall of the pipette tip. After a period of approximately 5–10 seconds, the beads were quantitatively (>95%) fixed to the wall. The supernatant was discarded and the beads could be washed by repeated pipetting of water or buffer. For the quantitative transfer of the beads into the reaction vessels, the experiment described in FIGS. 4a to 4d were tested. The washing procedure described in FIG. 4d proved to be particularly advantageous. The beads were first separated from the suspension contained in the pipette, and the liquid was ejected from the pipette. While the magnet is located at the pipette wall, thus fixing the beads in their position, washing water is drawn into the pipette. This washing water is again ejected from the pipette and another portion of fresh washing water is drawn in. Now, the pipette is slowly moved upwardly, so that the beads are transported into the tip of the pipette through the effects on the magnet. In step 7, the liquid is ejected from the pipette and takes along the beads located in the tip of the pipette. After this step, the pipette is again rinsed with washing water.

The references mentioned hereinabove are hereby incorporated by reference for the indicated disclosures thereof. Another method of magnetically separating components from a liquid, utilizing suspended magnetic particles, is disclosed in U.S. application Ser. No. 08/490,986, filed Jun. 15, 1995, now U.S. Pat. No. 5,837,144 in the name of Bienhaus et al., entitled "Methods of Magnetically Separating Liquid Components", (Attorney Docket No. 1614-5034), the disclosure of which is hereby incorporated by reference.

European published patent application No. EP-A-0557828 (Horiba) discloses a pipetting arm which can be used in the method and with the apparatus of the present invention. The disclosure of EP-A-0557828 is hereby incorporated by reference for the teachings of such pipetting arm therein, and for the disclosure of such arm with replaceable tips.

The magnetic microparticles used in the present invention will generally have a diameter between a few tenths of a micrometer and several micrometers, and preferably between 0.3 and 5 micrometers, more preferably of 0.5 to 3 micrometers. It is advantageous for the density of the microparticles to be as close as possible to the density of the liquid used in the separating process, in order to reduce the risk that separation due to gravity or buoyancy will occur. The density of the microparticles will generally be between 1.0 and 2.0 g/ml, and preferably is about 1.3 g/ml.

Figure 5:
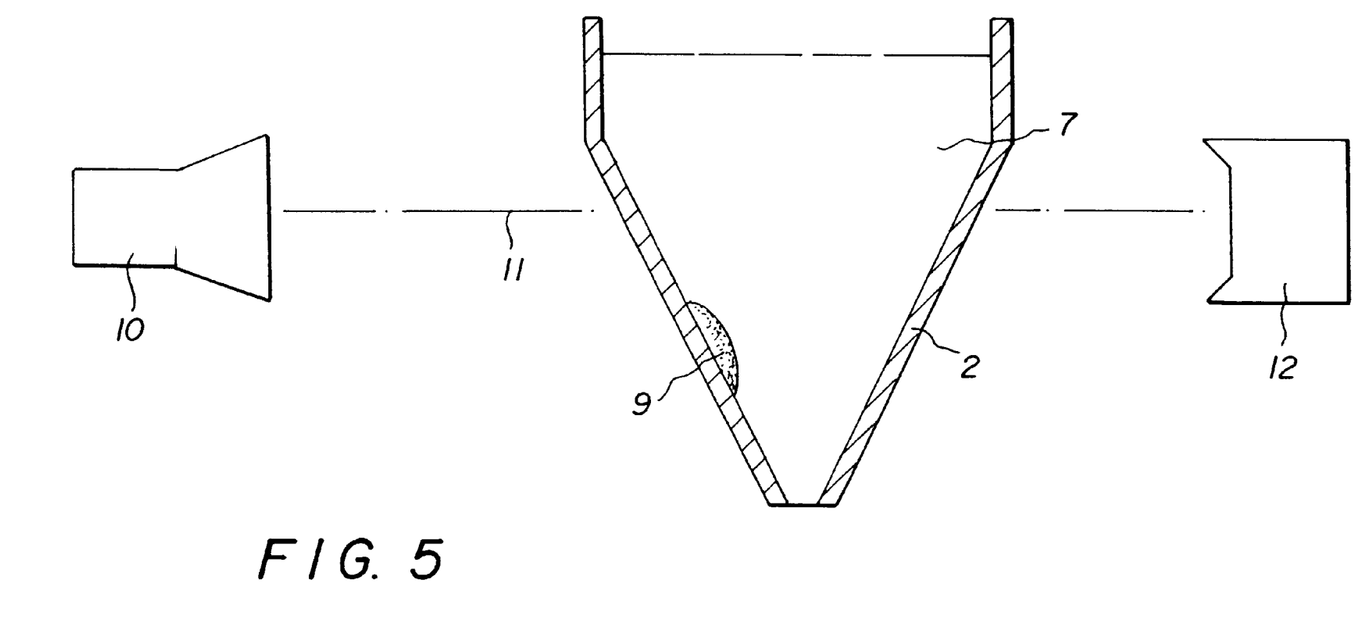
FIG. 5: Detection of microparticle separation.

FIG. 5 illustrates a modification of the present invention wherein the separation of the microparticles is detected to determine if complete separation has occurred. Light source 10 exposes the liquid 7 in pipette 2 to a light beam 11. A receiver 12 measures the amount of the light beam 11 passing through pipette 2 and liquid 7, and determines if all of the microparticles 9 have been separated using convention turbidity methods.

What is claimed is:

1. Device for separating magnetic microparticles from a suspension in a liquid, said device comprising:
   a pipette having an inner wall, said pipette containing a suspension of magnetic microparticles in a liquid therein, as pipette contents, wherein the pipette is configured to be rotatable about a longitudinal axis thereof;
   a pump connected to the pipette;
   a magnet exterior of the pipette and locateable to apply a magnetic field to at least part of the pipette contents to deposit the microparticles on the inner wall of the pipette; and
   moving means for causing relative movement of the pipette and the magnet to move at least one of them toward the other.

2. Device for separating magnetic microparticles from a suspension in a liquid, said device comprising:
   a pipette having an inner wall, said pipette containing a suspension of magnetic microparticles in a liquid therein as pipette contents;
   a pump connected to the pipette;
   a magnet exterior of the pipette and locateable to apply a magnetic field to at least part of the pipette contents to deposit the microparticles on the inner wall of the pipette; and
   moving means for causing relative movement of the pipette and the magnet to move at least one of them toward the other,
   wherein the magnet is configured to be movable around a longitudinal axis of the pipette.

3. Device of claim 1, wherein the pump is a vacuum pump.

4. Device of claim 1, wherein the moving means moves the pipette toward the magnet and also moves the pipette in a longitudinal direction.

5. Device of claim 1, wherein the pipette includes a tube having a tip on one end thereof.

6. Device of claim 1, further including separating means for separating magnetic particles, a radiation source for causing a light beam to traverse the contents of the pipette, and a receiver to detect the light radiation passing through the pipette contents from the radiation source.

7. Device of claim 4, wherein the moving means is a pipetting arm of an analysis instrument.

8. Device for separating magnetic microparticles from a suspension in a liquid, said device comprising:
   a pipette having an inner wall, said pipette containing a suspension of magnetic microparticles in a liquid therein, as pipette contents;
   a pump connected to the pipette;
   a magnet exterior of the pipette and locateable to apply a magnetic field to at least part of the pipette contents to deposit the microparticles on the inner wall of the pipette; and
   moving means for causing relative movement of the pipette and the magnet to move at least one of them toward the other,
   wherein said pipette, said magnet, and said moving means are configured such that the pipette and magnet are movable relative to one another in a direction of a longitudinal axis of the pipette from a first position wherein the magnet is proximate an upper level of liquid inside the pipette to a second position wherein the magnet is proximate the pipette tip, wherein the magnetic field deposits microparticles on the inner wall during an entire movement of the magnet from the first position to the second position, to collect magnetic microparticles deposited on the inner wall of the pipette in the pipette tip, and wherein the moving means moves the pipette and the magnet away from each other to release the magnetic microparticles from the magnetic field holding the magnetic microparticles against the inner wall of the pipette prior to ejection of the magnetic microparticles from the pipette tip.

9. Device of claim 2, wherein the pump is a vacuum pump.

10. Device of claim 2, wherein the moving means moves the pipette toward the magnet and also moves the pipette in a longitudinal direction.

11. Device of claim 2, wherein the pipette includes a tube having a tip on one end thereof.

12. Device of claim 2, further including separating means for separating magnetic particles, a radiation source for causing a light beam to traverse the contents of the pipette, and a receiver to detect the light radiation passing through the pipette contents from the radiation source.

13. Device of claim 10, wherein the moving means is a pipetting arm of an analysis instrument.

* * * * *